United States Patent
Ichinohe

(10) Patent No.: US 6,878,792 B2
(45) Date of Patent: Apr. 12, 2005

(54) DYE FOR AN INTRAOCULAR LENS AND AN INTRAOCULAR LENS USING IT

(75) Inventor: Takashi Ichinohe, Funabashi (JP)

(73) Assignee: Canon-Staar Co. Inc., Tokyo (JP)

( * ) Notice: Subject to any disclaimer, the term of this patent is extended or adjusted under 35 U.S.C. 154(b) by 0 days.

(21) Appl. No.: 10/236,584

(22) Filed: Sep. 5, 2002

(65) Prior Publication Data

US 2003/0078359 A1 Apr. 24, 2003

(30) Foreign Application Priority Data

Sep. 14, 2001 (JP) ........................................ 2001-279077

(51) Int. Cl.$^7$ .............................................. C08G 77/26
(52) U.S. Cl. ............................. 528/28; 528/31; 528/43; 528/32; 525/474; 548/125; 534/753; 534/839
(58) Field of Search ............................... 528/31, 43, 32, 528/28; 525/474; 548/125; 534/753, 839

(56) References Cited

U.S. PATENT DOCUMENTS 5,470,932 A * 11/1995 Jinkerson .................... 526/312

FOREIGN PATENT DOCUMENTS

| JP | H01-299560 | 12/1989 |
| JP | H08-503997 | 4/1996 |
| JP | H09-187500 | 7/1997 |

* cited by examiner

Primary Examiner—Kuo-Liang Peng
(74) Attorney, Agent, or Firm—Ladas & Parry LLP

(57) ABSTRACT

The present invention provides lenses for eyes having visible light transmission properties near to those of human crystalline lenses, particularly coloring techniques effective for soft lenses for eyes. The present invention is a yellow dye capable of chemical bonding to a silicone which is a material of the intraocular lens or capable of copolymerizing with a radical polymerizable monomer which is a material of the intraocular lens.

35 Claims, 1 Drawing Sheet

DYE FOR AN INTRAOCULAR LENS AND AN INTRAOCULAR LENS USING IT

TECHNICAL FIELD

The present invention relates to synthesis of a polymer chemically bonded to a yellow dye, and use thereof in an intraocular lens. Particularly, it relates to a yellow dye capable of chemical bonding to a silicone which is a material of the intraocular lens or capable of copolymerizing with a radical polymerizable monomer which is a raw material of the intraocular lens.

BACKGROUND ART

Lately, influences of a blue violet light on human body are reported, in these influences, injuries to eyes, particularly, light harm to the retina are feared. Intraocular lenses which are inserted in eyes after an operation for cataract, contact lenses, implants of the cornea and other intraocular lenses should have functions for guarding against rays having such high energy. The sun is emitting ultraviolet, visible rays, infrared in large quantities. The sun emission, which arrives on the surface of the earth through the atmosphere, constitutes UV-B (230–300 nm), near ultraviolet or UV-A (300–400 nm), visible rays (400–700 nm) and near infrared rays (700–1400 nm). The choroid of human mostly transmits near infrared rays and visible spectrum under common conditions. However, the cornea mostly absorbs UV-B so that the UV-B can not attain to the retina.

The senility changes of transmission properties of ultraviolet and visible rays appear in the human crystalline lenses by aging. The crystalline lenses freely transmit ultraviolet and visible rays in infancy, less transmit the rays with age, and become yellowish gradually. Particularly, as the transmissivity of rays between 400 nm and 500 nm slowly lower, visible view becomes yellowish. The visual function then becomes habituated to such conditions. By the reason, when the crystalline lenses of aged patients of cataract are cut out and transparent artificial lenses are inserted into the eyes, protective reactions of eyes, especially tissues of the retina and the like in fundus oculi, to protect from ultraviolet and near ultraviolet rays are lowered. As a result, the patient feels bluish view after the surgical operation. It is called Chromatopsia.

In recent years, lenses for eyes to protect from harmful ultraviolet, particularly intraocular lenses are available in markets. These lenses are produced by mixing or chemical bonding of an ultraviolet absorber, which cuts off lights of less than 400 nm, with a lens material, to lower the amount of incident ultraviolet to the eyes and protect the eyes from the harmful ultraviolet. Further, colored intraocular lenses are available in markets. These lenses are produced by mixing or copolymerizing an ultraviolet absorber and a dye, which has absorption at a visible short wave range, with a material of hard lenses. On the other hand, as the materials of intraocular lenses other than those of hard lenses, lenses produced by soft materials such as silicone elastomers and acrylic elastomers can be obtained at a market. When a dye is directly mixed or dispersed into these soft materials, there is a possibility of breeding out of the dye because of high molecular motion of the materials themselves. Accordingly, in case of the production of colored lenses with soft materials, the colored molecules should be rigidly bonded to the polymer of the materials.

Japanese Patent Laid-open Publication H01-299560 discloses a material for an intraocular lens characterizing in a polymerizable ultraviolet absorber having polymerizable groups selected from the groups comprising of acryloyl, methacryloyl, vinyl, allyl and isopropenyl and a polymerizable dye having polymerizable groups selected from the groups comprising of acryloyl, allyl and isopropenyl, which copolymerizes with another polymerizable monomer ingredient for lens production. Japanese Patent Laid-open Publication H08-503997 discloses a polymer lens material for eyes, which contains one or more monomers for forming lenses selected from the groups comprising of acrylate monomers and methacrylate monomers and one or more polymerizable yellow dyes having one to four polymerizable acrylate or methacrylate groups, wherein the dye part is substituted for each acrylate or methacrylate group by a spacer group of the following formula [III].

[Chem. 4]

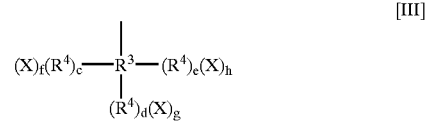

wherein $R^3$ is alkyl of less than 6 carbons; $R^4$ is a noncyclic organic spacer of less than ten atoms of C, H, Si, O, N, P, S, Cl, Br or F or a combination thereof; X is O, NH or $NR^5$, wherein $R^5$ is alkyl of $C_1$–$C_{10}$; d, e, g and h are independently integers of 0–4; and c and f are independently integers of 1–4.

Further, Japanese Patent Laid-open Publication H09-187500 discloses diacrylates/dimethacrylates of the following formula [IV].

[Chem. 5]

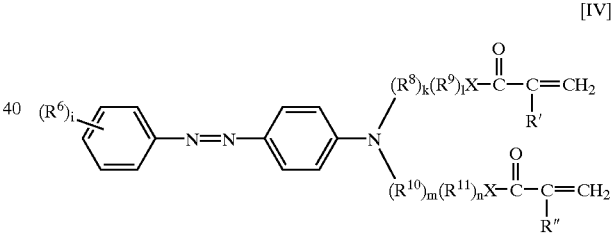

wherein R' and R" are independently H or $CH_3$, $R^6$ and $R^7$ are independently hydrogen, alkyl of $C_1$–$C_{20}$, $OCH_3$, $OC_2H_5$, $OC_3H_7$, or $OC_4H_9$, i and j are independently integers of 1 or 2, $R^8$, $R^9$, $R^{10}$ and $R^{11}$ are independently noncyclic organic spacer groups of less than 10 atoms, the spacer groups being C, H, Si, O, N, P, S, Cl, Br or F or combinations thereof, k and m are independently integers of 1–6, l and n are independently integers of 0–6, X is O, NH or $NR^5$, wherein $R^5$ is alkyl of $C_1$–$C_{10}$.

These techniques disclosed in known references apply a method for copolymerizing a polymerizable coloring agent or an ultraviolet absorbing agent with an acrylic or methacrylic polymer by radical polymerization. Materials of the colored intraocular lenses produced by these techniques are hard polymethylmathacrylate. Although the above known techniques take effect to provide stable hard lenses, there are many problems because a suitable method for coloring soft intraocular lenses and a technique therefor are not disclosed. Moreover, since azo dyes generally inhibit radical polymerization, there is the possibility of remains of unpolymerized monomers or low molecular ingredients in polymer products. Some claims of these patent applications disclose dyes having a phenolic hydroxyl group. However, since the phenolic hydroxyl group traps growth radicals in the polymerization, it is not suited for radical polymerization. Some claims of these patent applications disclose dyes using an allyl group as a polymerizable group. The allyl group is poor in radical polymerization and unsuitable for such polymerization. Monomers having acryl or methacryl groups have high reactivity and high toxicity, so that these are difficult to treat.

The present invention provides lenses for eyes having visible light transmission properties near to those of human crystalline lenses, particularly coloring techniques effective for soft lenses for eyes.

The present invention is a dye having a constitution of the following formula [I] or [II].

[Chem. 6]

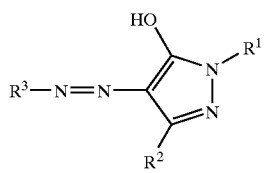

wherein $R^1$ is linear or branched alkyl of $C_1$–$C_{10}$, or phenyl; when $R^1$ is phenyl, one or more hydrogens of its aromatic ring may be substituted by linear or branched alkyl of $C_1$–$C_{10}$, linear or branched alkoxyl of $C_1$–$C_{10}$, hydroxy, amino, sulfo, nitro, halogen, carboxy, —C(=O)—O—$R^4$ or —C(=O)—NH—$R^4$ wherein $R^4$ is linear or branched alkyl of $C_1$–$C_{10}$, $R^2$ is linear or branched alkyl of $C_1$–$C_{10}$, amino or phenyl; when $R^2$ is amino, one or both hydrogens thereof may be substituted by linear or branched alkyl of $C_1$–$C_{10}$; or when $R^2$ is phenyl, one or more hydrogens of its aromatic ring may be substituted by linear or branched alkyl of $C_1$–$C_{10}$, linear or branched alkoxyl of $C_1$–$C_{10}$, hydroxy, amino, sulfo, nitro, halogen, carboxyl, —C(=O)—O—$R^4$, —C(=O)—NH—$R^4$ wherein $R^4$ is linear or branched alkyl of $C_1$–$C_{10}$, $R^3$ is phenyl or naphthyl, one or more hydrogens thereof are linear or branched alkyl of $C_1$–$C_{10}$, linear or branched alkoxyl of $C_1$–$C_{10}$, hydroxy, amino, sulfo, nitro, halogen, carboxy, —C(=O)—O—$R^4$, —C(=O)—NH—$R^4$, wherein $R^4$ is linear or branched alkyl of $C_1$–$C_{10}$, and in formula [I], at least one hydrogen of the aromatic ring constituted in $R^1$, $R^2$ or $R^3$ is substituted by any of $CH_2$=CH—$(CH_2)_m$—, $CH_2$=CH—$(CH_2)_m$—$X^1$—$(CH_2)_n$—, $CH_2$=C($R^5$)—$(CH_2)_m$—$X^1$—C(=O)—$(CH_2)_n$—, $CH_2$=C($R^5$)—$(CH_2)_m$—C(=O)—$X^1$—$(CH_2)_n$—, {$CH_2$=C($R^5$)—$(CH_2)_m$—}$_2$N—$(CH_2)_n$—, or {$CH_2$=C($R^5$)—$(CH_2)_m$—}$_2$N—C(=O)—$(CH_2)_n$—;

wherein $X^1$ is —O— or —$NR^6$—, $R^5$ and $R^6$ are independently hydrogen, or linear or branched alkyl of $C_1$–$C_{10}$, and m and n are independently integers of 0 to 10.

[Chem. 7]

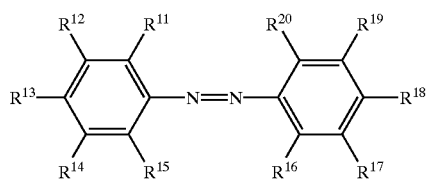

wherein $R^{11}$, $R^{12}$, $R^{13}$, $R^{14}$, $R^{15}$, $R^{16}$, $R^{17}$, $R^{18}$, $R^{19}$, and $R^{20}$ are independently selected from hydrogen, hydroxy, halogen, or linear or branched alkyl of $C_1$–$C_{10}$, and at least one of them is a substituted group represented by:

[Chem. 8]

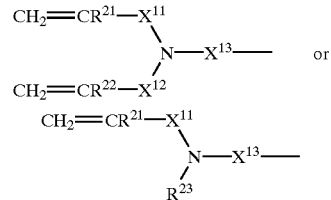

wherein $R^{21}$ and $R^{22}$ are independently hydrogen or methyl, $R^{23}$ is hydrogen or linear or branched alkyl of $C_1$–$C_{10}$, $X^{11}$, $X^{12}$ and $X^{13}$, independently, have covalent bonds, or linear or branched bivalent spacer groups, or —$(CH_2)_m$—O—$(CH_2)_n$—, wherein m and n are independently integers of 0 to 10.

The present invention is also a coloring silicone material which is obtained from chemical bonding of the dye represented by formula [I] or [II] of claim 1 to a silicone polymer having hydrosilyl groups.

The present invention is further a coloring silicone material using a material which is obtained from chemical bonding of the dye represented by formula [I] or [II] of claim 1 and a ultraviolet absorber having functional groups capable of chemical bonding, to a silicone having hydrosilyl groups.

The yellow dye of the present invention has a constitution able to bond chemically to transparent silicone having hydrosilyl groups by an addition reaction. Since the dye is possible to directly attach to polymer chains, it very less exude from materials after shaping for the use in the eyes. As the yellow dye of the present invention has also radical polymerizability, it is possible to obtain colored intraocular lenses by copolymerization with monomers of radical polymerizability such as acrylic and styrene types. More preferably, the lens materials are obtained by using a method other than radical polymerization, namely by bonding the dye to a polymer chain. The yellow dyes of the present invention have a maximum absorption of 350–450 nm, lenses for eyes, which are obtained by bonding both of the yellow dye and another ultraviolet absorbing agent to silicone or by copolymerization of the dye with a monomer constituting lenses, can shut off the greater part (more than 99%) of incident violet lights to the eyes and lower blue light intensity to reduce bad influence of light to eyes. The lenses can be used as intraocular lenses, glasses, contact lenses and the other lenses for eyes.

The colored silicone obtained by the present invention has its absorption band in the blue region. The silicone does not exude the dye from the material, and it has suitability to living organisms, so that it is possible to fit into eyes in the long term.

BEST EMBODIMENT FOR CARRYING OUT INVENTION

Figure 1:
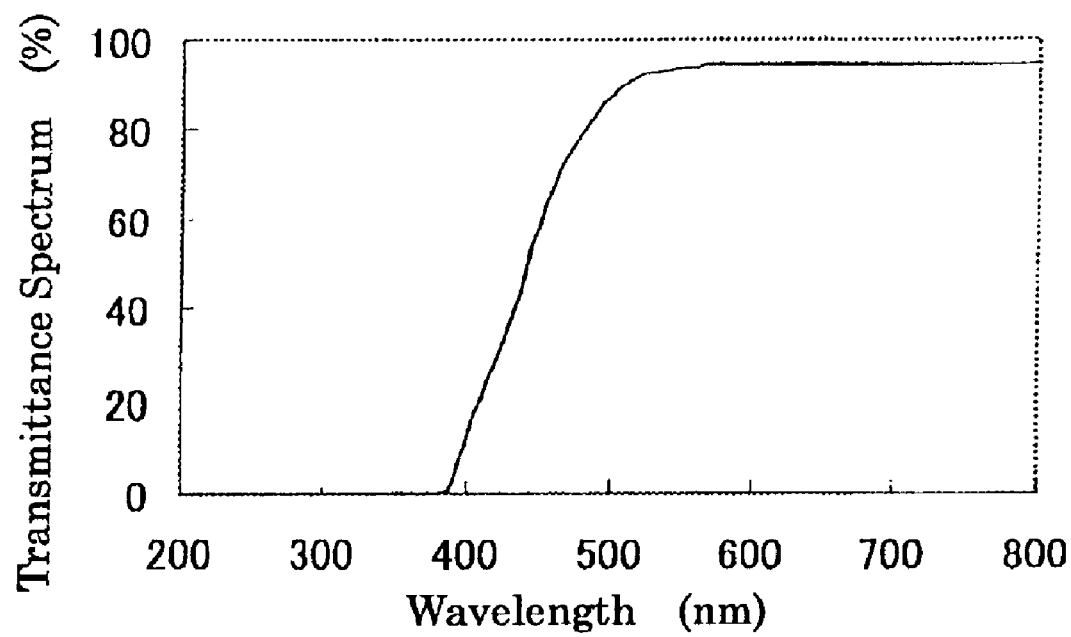
FIG. 1 shows a transmittance spectrum of the ultraviolet-visible light of the plate sample of silicone elastomer in Example 1.

The yellow dye of the present invention, which has possibility of addition bonding to silicone, has a basic skeleton of azobenzene or phenylazopyrazolone, and it has unsaturated alkyl groups such as vinyl and allyl, which has possibility of addition bonding to silicone polymers. Moreover, similarly, it has characteristics of cut-off of violet light and protection of eyes from not only blue light but also violet light by using a supporting mixture of the dye and an ultraviolet absorbing agent having possibility of addition bonding to silicone at the same time, or by using a mixture of the dye and silicone supporting an ultraviolet absorbing agent.

A form of the yellow dye of the present invention is represented by a constitution of an enol type of the above general formula [I], and also by a keto type of the formula.

Examples of such compounds are 4-(4-acryloyloxyphenyl)azo-3-methyl-1-phenyl-5-pyrazolone, 4-(4-methacryloylphenyl)azo-3-methyl-1-phenyl-5-pyrazolone, 4-(4-methacryloyloxyphenyl)azo-3-methyl-1-phenyl-5-pyrazolone, 3-methyl-1-phenyl-4-(4-vinylphenyl)azo-5-pyrazolone, 1-(4-tert-butylphenyl)-3-methyl-4-(4-vinylphenyl)azo-5-pyrazolone, 4-(4-allylphenyl)azo-3-methyl-1-phenyl-5-pyrazolone, 4-(4-hydroxy-3-allylphenyl)azo-3-methyl-1-phenyl-5-pyrazolone, 4-allyloxyphenylazo-3-methyl-1-phenyl-5-pyrazolone, 4-(4-allyloxymethylphenyl)azo-3-methyl-1-phenyl-5-pyrazolone, 4-allyloxycarbonylphenylazo-3-methyl-1-phenyl-5-pyrazolone, 4-(4-allyloxycarbonylphenyl)azo-3-methyl-1-phenyl-5-pyrazolone, 4-(4-allylphenyl)azo-1-(4-tert-butylphenyl)-3-methyl-5-pyrazolone, 4-(4-allyloxyphenyl)azo-1-(4-tert-butylphenyl)-3-methyl-5-pyrazolone, 4-(4-allyloxycarbonylphenyl)azo-1-(4-tert-butylphenyl)-3-methyl-5-pyrazolone, 4-(4-acryloylphenyl)azo-1-(4-tert-butylphenyl)-3-methyl-5-pyrazolone, 4-(4-acryloyloxyphenyl)azo-1-(4-tert-butylphenyl)-3-methyl-5-pyrazolone, 1-(4-tert-butylphenyl)-4-(4-methacryloylphenyl)azo-3-methyl-5-pyrazolone, 1-(4-tert-butylphenyl)-4-(4-methacryloyloxyphenyl)azo-3-methyl-5-pyrazolone, 1-(4-allylphenyl)-3-methyl-4-phenylazo-5-pyrazolone, 1-(4-allylphenyl)-4-(4-tert-butylphenyl)azo-3-methyl-5-pyrazolone, 1-(4-allyloxyphenyl)-4-(4-tert-butylphenyl)azo-3-methyl-5-pyrazolone, 1-(4-allyloxycarbonylphenyl)-4-(4-tert-butylphenyl)azo-3-methyl-5-pyrazolone, 1-(4-allylphenyl)-4-(2-tert-butylphenyl)azo-3-methyl-5-pyrazolone, 1-(4-allylphenyl)-4-(4-sec-butylphenyl)azo-3-methyl-5-pyrazolone, 1-(4-allylphenyl)-4-(2-tert-butylphenyl)azo-3-methyl-5-pyrazolone, 1-(4-allylphenyl)-4-(2-sec-butylphenyl)azo-3-methyl-5-pyrazolone, 1-(4-acryloylphenyl)-3-methyl-4-phenylazo-5-pyrazolone, 4-(3-methyl-1-phenyl-5-pyrazolone-4-yl)azoallylanilido, 4-(3-methyl-1-phenyl-5-pyrazolone-4-yl)azoallylanilido, N-allyl-4-(3-methyl-1-phenyl-5-pyrazolone-4-yl)azobenzamide, N,N-diallyl-4-(3-methyl-1-phenyl-5-pyrazolone-4-yl)azobenzamide and the like, but these are not limited to the above compounds.

The yellow dye of the present invention also has general formula [II] in addition to the above general formula [I].

Examples of such compounds are N,N-diallyl-4-aminoazobenzene, N-allyl-4-aminoazobenzene, 4-allyloxymethylazobenzene, N,N-dimethacryl-4-aminoazobenzene, N-methacryl-4-aminoazobenzene, 4-methacryloxymethylazobenzene, N,N-diallyl-4-(2-aminoethyl)azobenzene, N,N-diallyl-4-aminomethylazobenzene, N-allyl-4-(2-aminoethyl)azobenzene, N-allyl-4-aminomethylazobenzene, N,N-diethyl-4-amino-3-allylazobenzene, N,N-dimethyl-4-amino-3-allylazobenzene, N,N-diethyl-4-amino-4'-allylazobenzene, N,N-dimethyl-4-amino-4'-allylazobenzene and the like, but these are not limited to the above compounds.

Examples of the dye of the present invention are preferably the following compounds 1, 2, 3 and 4.

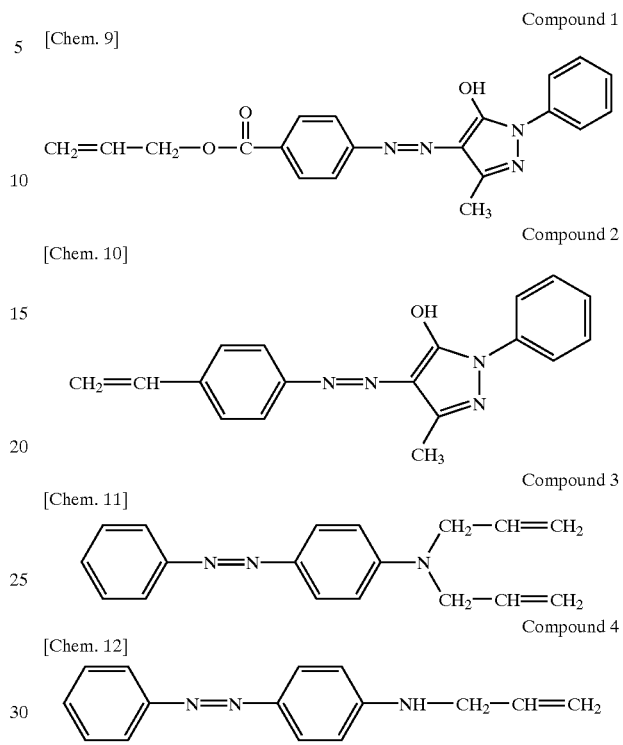

Compounds 1, 2, 3 and 4 have a possibility of covalent bonding of a silicone polymer, by an addition reaction of the end C═C bonds themselves with hydrosilyl groups of silicone having the hydrosilyl groups. Because of the reaction, dye exudates from such obtained materials are very little. Further it is possible to introduce these compounds into the polymer produced by radical polymerization.

The above dye compounds have a maximum absorbance of about 350–450 nm. Some of them have a weak absorbance at less than 350 nm. In such compounds, another ultraviolet absorbing agent should be preferably used at the same time. There are several types of ultraviolet absorbing agents, such as benzophenone, benzotriazole, salicylic acid and indole types, but are not limited. It is important that these types are used for compensating the absorbance of the above dyes and have functional groups which are able to chemically bind to silicone to be main materials of lenses.

Examples of such ultraviolet absorbing agents are 2-(5-acryloyloxyethyloxy-2-hydroxy-3-tert-butylphenyl)-2H-benzotriazol, 2-(2-hydroxy-5-acryloyloxyphenyl)-2H-benzotriazole, 2-(2-hydroxy-4-methacryloyloxyethoxy)-4-chloro-2H-benzotriazole, 2-(2-hydroxy-3-tert-butyl-5-vinylphenyl)-5-chloro-2H-benzotriazole, 2-(3-allyl-2-hydroxy-5-methylphenyl)-2H-benzotriazole, 2-(3-allyl-2-hydroxy-5-tert-butylphenyl)-2H-benzotriazole, 2-hydroxy-4-methacryloyloxybenzophenone, 2-hydroxy-4-methacryloyloxyethoxybenzophenone, 4-acryloyloxy-2-hydroxybenzophenone, 4-acryloyloxyethoxy-2-hydroxybenzophenone and the like, but these are not limited.

By using the yellow dye of the present invention having a possibility of addition reaction to silicone having hydrosilyl groups, the addition reaction using a catalyst such as platinum can provide a silicone compounds having a very little fear of elution of the dye directly bound to the silicone.

Examples of the above silicone compounds having hydrosilyl groups are dimethylsiloxane-methylhydrosiloxane copolymer, diphenylsiloxane-phenylhydrosiloxane copolymer, polyethylhydrosiloxane, methylhydrosiloxane-phenylmethylsiloxane copolymer, methylhydrosiloxane-octylmethylsiloxane copolymer, methyl silicone resin containing hydrosilyl groups, polyphenyl(dimethylhydrosiloxy)siloxane and the like, but these are not limited.

Catalysts using in the addition reaction of yellow dyes to silicone compounds are desirably platinum compounds such as hydrogen chloroplatinate, platinum-divinyltetramethyldisiloxane, and platinum-tetramethyltetravinylcyclosiloxane.

Further, a silicone bound to the yellow dye obtained by the above method provides a silicone elastomer chemically bound to the yellow dye by crosslinking with a silicone having vinyl groups.

Further, a silicone bound to the above yellow dye provides a silicone elastomer chemically bound to the yellow dye by crosslinking with a mixture of silicone having vinyl groups and silica.

To form the above elastomer, catalysts such as platinum compounds such as hydrogen chloroplatinate, a platinum-divinyltetramethyldisiloxane complex, a platinum-tetramethyltetravinylcyclotetrasiloxane complex and a platinum-alumina supporting catalyst can be used, and such catalysts provide a smooth crosslinking reaction.

The yellow dye of the present invention can be chemically bound to silicone having hydrosylil groups and then crosslinked with silicone having vinyl groups. The other method is that the yellow dye of the present invention is mixed with silicone having hydrosilyl groups or silicone having vinyl groups, and the mixture is mixed with silicone having hydrosilyl groups and silicone having vinyl groups, and then the mixture is cross-linked at the same time the yellow dye is reacted to the hydrosilyl groups.

At the mixing with silicone described above, it is preferable to homogeneously disperse the yellow dye by using an appropriate solvent. As such solvents, acetone, ethanol, methanol, tetrahydrofuran, dichloromethan can be exemplified. To the solvent, the yellow dye is dissolved and mixed with silicone. Then, the solvent is distilled away with an evaporator, and the yellow dye can be uniformly dispersed in silicone.

EXAMPLES

The following is synthetic examples of the compounds of the present invention and embodiment examples of the present invention.

Synthetic Example 1

Synthesis of Compound 1

1. Synthesis of Diazonium Benzoate

P-amino benzoic acid 6.86 g (0.05 mol) was placed in a three necked flask of 1000 ml, 1 mol/l of hydrochloric acid 100 ml was added to dissolve the mixture. A mechanical stirrer, a thermometer and a dropping funnel of 200 ml were attached to the three-necked flask. The flask was placed in an ice bath, and the temperature in the flask was kept at 0–5° C. Sodium nitrite ($NaNO_2$) 3.8 g (0.055 mol) was dissolved in 10 ml of distilled water, and the solution was slowly added dropwise from the neck into the flask for five minutes. The temperature in the flask was kept at 0–5° C., stirring was continued for 30 minutes, and yellow liquid was obtained to use for next reaction.

2. Synthesis of 4-(4'-carboxyphenylazo)-3-methyl-1-phenylpyrazolone by azo coupling reaction 3-Methyl-1-phenylpyrazolone 10.45 g (0.06 mol) was dissolved in 1 mol/l of aqueous solution of sodium hydroxide 100 ml and the solution was placed into the above dropping funnel. Vigorously stirring with a magnetic stirrer, the above aqueous solution was slowly added dropwise for one hour while it was kept at 0–5° C. After all solution was dropped, 1 mol/l of aqueous solution of sodium hydroxide 100 ml was added, and the mixture was stirred for more two hours. After the reaction was finished, hydrochloric acid was added dropwise at room temperature, and 2N hydrochloric acid was slowly added dropwise to obtain a reaction solution of pH 2 with a monitor of pH test paper. A large quantity of a precipitate was produced. The precipitate was filtered with Buchner funnel suction. The precipitate was washed with distilled water until pH of the filtrate was changed to 7. The suction was continued until the filtrate was not obtained, and the residue was washed with acetone 500 ml. The precipitate was placed in a heat dryer of 60° C. and was dried under reduced pressure overnight with a vacuum pump.

3. Synthesis of 4-(4'-allyloxycarbonylphenylazo)-3-methyl-1-phenylpyrazolone

Dried solid 5 g was collected from the above precipitate and placed in an oval flask of 300 ml. Thionyl chloride 50 ml was added, and a ball tipped cooler was attached to the flask. The flask was kept in an oil bath at 90~100° C., and the mixture was reacted for 30 minutes. After the reaction was finished, thionyl chloride was distilled away under reduced pressure. Allyl alcohol 50 ml and pyridine 5 ml were added into the flask, and the mixture was stirred for 30 minutes at the oil bath temperature of 90–100° C. and cooled to room temperature. The reaction solution was placed in a separatory funnel of 1000 ml, and dichloromethan 100 ml and distilled water 100 ml were added. The solution was separated into two layers, and water of the upper layer and organic layer of the lower layer were appeared. The lower organic layer was taken out of the funnel and washed with distilled water 100 ml, washed with 1 mol/l of aqueous solution of sodium hydroxide 100 ml three times, and washed with distilled water three times. It was confirmed with a pH test paper that the water layer was changed into neutral. The organic layer solution was taken out, after magnesium sulfate 5 g was added to the solution, the mixture was stirred for 3 minutes. Magnesium sulfate was filtered off without suction. Solvent was distilled away with an evaporator to obtain orange solid. The obtained solid was dissolved in methanol 200 ml and the mixture was submitted to heat filtration and cooled. Needle crystals separated out slowly and were left for about one hour in a refrigerator. The obtained needle crystals were separated by filtration, and dried in vacuo to obtain the crystals of the desired compound.

$^1$H-NMR: δ=2.4, 4.8, 5.3–5.5, 6.0–6.1, 7.2–7.3, 7.4, 7.9, 8.1, 13.5 ppm

FT-IR: 3060, 1719, 1561, 1550, 1499, 1251, 1159, 1108, 765 $cm^{-1}$

Synthetic Example 2

Synthesis of Compound 2

1. Synthesis of a diazonium salt of 4-aminostyrene

1 N hydrochloric acid 100 ml was placed into a 1000 ml three necked flask equipping with a thermometer, and 4-aminostyrene 2.5 g was added and dissolved. Ice cooling the flask, an aqueous solution 10 ml of sodium nitrite 1.45 g was slowly added for about ten minutes. All reaction solution was changed into green brown.

2. Synthesis of 3-methyl-1-phenyl-4-(4-vinylphenylazo)-5-pyrazolone by azo coupling reaction 3-methyl-1-phenylpyrazolone 3.7 g was dissolved in 1 N aqueous solution 200 ml of sodium hydroxide. The solution was placed in a dropping funnel, and slowly added dropwise for about one hour into the solution prepared in above 1. With dropping, a red brown precipitate was produced in the solution. After the dropping was finished, the solution was warmed to room temperature, and stirred for one hour. Measuring with a pH meter, 1 N hydrochloric acid was added to obtain a solution of pH 2. The solution was filtered with suction, and the precipitate was obtained. The precipitate was washed well with water, and dried in vacuo overnight.

3. Preparation of 3-methyl-1-phenyl-4-(4-vinylphenylazo)-5-pyrazolone

Toluene 100 ml was added into the solid obtained in the above 2, and the mixture was heated to 70–80° C. and dissolved. The mixture was filtered without suction with filter paper to filter off impurities. After removing toluene with an evaporator, the residue was dried and recrystallized from small amounts of methanol to obtain needle crystals of aimed compound.

$^1$H-NMR: δ=2.4, 5.3, 5.7, 6.7, 7.2–7.3, 7.4–7.5, 8.0, 13.7 ppm

FT-IR: 3060, 3006, 2921, 1654, 1582, 1550, 1501, 1490, 1341, 1270, 1155, 994, 913, 753 cm$^{-1}$

Synthetic Example 3

Synthesis of Compound 3

4-aminoazobenzene 1 g was dissolved in a mixture of ethanol 40 ml and toluene 5 ml in an oval flask of 200 ml, and allyl bromide 10 ml was added. The flask was immersed in an oil bath at 80° C. and heated to reflux the mixture for 30 minutes. Then, by adding NaOH 2 g, the color of the solution was changed into greenish yellow. Allyl bromide 10 ml was further added, and the mixture was refluxed at 80° C. for 30 minutes. After the reaction was finished, dichloromethan 100 ml was added, and the solution was washed with 1N NaOH aqueous solution three times and water 100 ml three times. The dichloromethane layer was taken out and the solvent was distilled away with an evaporator. After adding a small amount of ethanol, the mixture was submitted to heat filtration and cooled in a refrigerator. Needle crystals separated out. The obtained crystals were filtered and dried in vacuo to obtain crystals of the aimed compound.

Embodying examples of the present invention are shown below.

Example 1

Production of Colored Silicone with Compound 1

Compound 1 0.01 g, 2-hydroxy-4-methacryloyloxyethoxybenzophenone 0.5 g commercially available as an ultraviolet absorber, and KE-103 100 g (manufactured by Shinetu Silicone, principal constituent: vinyl-terminated polydimethylsiloxane) which is a transparent silicone of a two-part hard type commercially available as a principal material, these three compounds were mixed with stirring to make uniform compound 1 and the ultraviolet absorber. To the resulting principal material of silicone that compound 1 and the ultraviolet absorber were uniformly dispersed, CAT-103, which is a silicone-crosslinking agent attached to KE-103, was mixed in the weight ratio of 1/10 per silicone. After removing bubbles by vacuum degassing, the mixture was interposed with glass plates and heat cross-linked at 100° C. for 30 minutes to obtain a plate sample of a colored silicone elastomer. FIG. 1 shows a transmittance spectrum of the ultraviolet-visible light of the plate sample.

Example 2

Production of Colored Acrylic Resin with Compound 2

Compound 2 0.01% by weight, phenylethylacrylate 60% by weight, phenylethylmethacrylate 34% by weight, 1,3-propanedioldiacrylate 3.5% by weight, 2-(2-hydroxy-5-acryloyloxyphenyl)-2H-benzotriazol 1.5% by weight, AIBN 1% by weight as an initiator, these materials were mixed. The mixture was interposed with glass plates and polymerized at 100° C. for 2 hours. After extracting unreacted materials from the polymer with acetone by a Soxhlet's extractor, the polymer was dried in vacuo to obtain an acrylic plate sample.

Examples 3

Production of Colored Silicone with Compound 3

Figure 2:
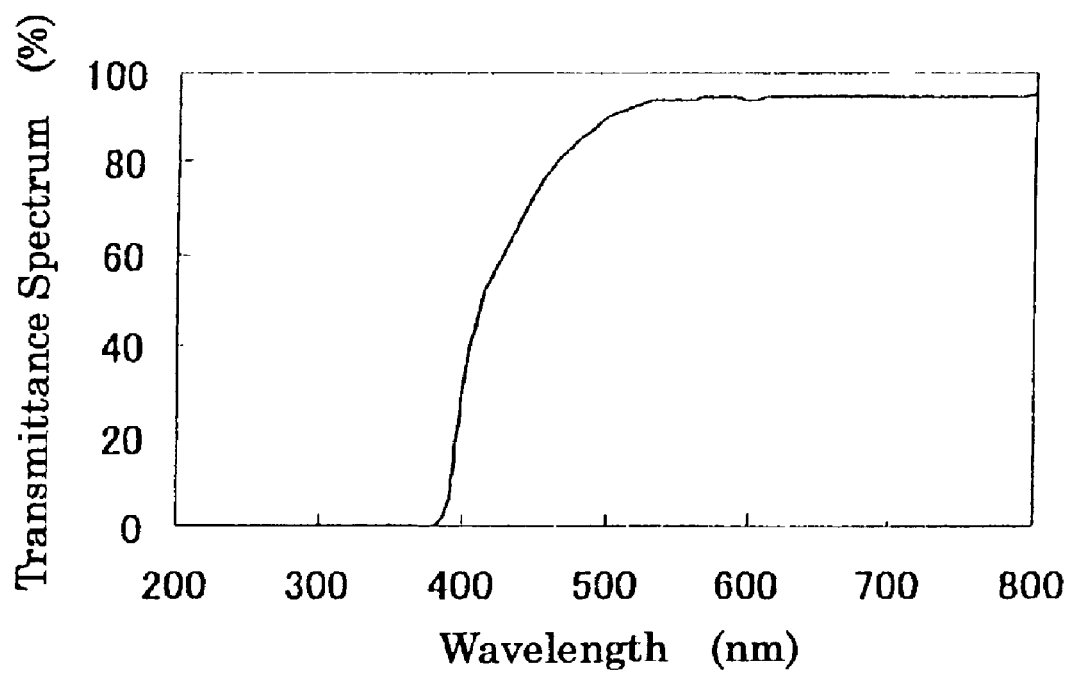
FIG. 2 shows a transmittance spectrum of the ultraviolet-visible light of the plate sample of silicone elastomer in Example 3.

To 100 g of commercially available trimethylsilyl-terminated dimethylsiloxane-methylhydrosiloxane copolymer (Aldorich) which was heated to 90° C., 0.1 g of compound 3 and 5 g of 2-hydroxy-4-methacryloyloxyethoxybenzophenone was added, and a commercial complex of platinum-divinyltetramethyldisiloxane (Aldorich) was added to obtain platinum concentration of 5 ppm. The mixture was reacted at 80° C. for one hour. After cooling the reactant, filtration was conducted with a 0.5μ membrane filter to obtain an orange silicone cross-linking agent. The colored silicone cross-linking agent was mixed with KE-103 (manufactured by Sinetsu silicone, principal constituent : vinyl-terminated polydimethylsiloxane) in the ratio of 1/10 per the principal material. After removing bubbles by vacuum degassing, the mixture was interposed with glass plates and heat cross-linked at 100° C. for 30 minutes to obtain a plate sample of a colored silicone. FIG. 2 shows a transmittance spectrum of the ultraviolet-visible light of the plate sample.

Comparative Example 1

C.I. Solvent Yellow 16 of a commercial dye 0.01 g, 2hydroxy-4-methacryloyloxyethoxybenzophenone of a commercial polymerizable ultraviolet absorber 0.1 g, a transparent silicone 100 g of a commercial two-part hard type as a principal material, these materials were mixed with stirring to make uniform the dye and the ultraviolet absorber. The resulting principal material of colored silicone and a usual silicone cross-linking agent were mixed with a suitable mixing ratio. The mixture was interposed with glass plates and heat cross-linked to obtain a plate sample of a colored silicone elastomer. Since thus obtained colored silicone elastomer easily exuded the dye on the surface, it was not appropriate for use as a material of living organisms.

What is claimed is:

1. A coloring silicone material which is obtained from chemical bonding of the dye represented by formula [I] or [II] to a silicone polymer having hydrosilyl groups; wherein formula [I] is represented by the general formula:

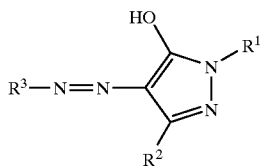

[I]

wherein $R^1$ is linear or branched alkyl of $C_1$–$C_{10}$, or phenyl; when $R^1$ is phenyl, one or more hydrogens of its aromatic ring may be substituted by linear or branched alkyl of $C_1$–$C_{10}$, linear or branched alkoxyl of $C_1$–$C_{10}$, hydroxy, amino, sulfo, nitro, halogen, carboxy, —C(=O)—O—$R^4$ or —C(=O)—NH—$R^4$, wherein $R^4$ is linear or branched alkyl of $C_1$–$C_{10}$, $R^2$ is linear or branched alkyl of $C_1$–$C_{10}$, amino or phenyl; when $R^2$ is amino, one or both hydrogens thereof may be substituted by linear or branched alkyl of $C_1$–$C_{10}$; or when $R^2$ is phenyl, one or more hydrogens of its aromatic ring may be substituted by linear or branched alkyl of $C_1$–$C_{10}$, linear or branched alkoxyl of $C_1$–$C_{10}$, hydroxy, amino, sulfo, nitro, halogen, carboxyl, —C(=O)—O—$R^4$, —C(=O)—NH—$R^4$ wherein $R^4$ is linear or branched alkyl of $C_1$–$C_{10}$, $R^3$ is phenyl or naphthyl, one or more hydrogens thereof are linear or branched alkyl of $C_1$–$C_{10}$, linear or branched alkoxyl of $C_1$–$C_{10}$, hydroxy, amino, sulfo, nitro, halogen, carboxy, —C(=O)—O—$R^4$, —C(=O)—NH—$R^4$, wherein $R^4$ is linear or branched alkyl of $C_1$–$C_{10}$, and in formula [I], at least one hydrogen of the aromatic ring constituted in $R^1$, $R^2$ or $R^3$ is substituted by any of $CH_2=CH-(CH_2)_m-$, $CH_2=CH-(CH_2)_m-X^1-(CH_2)_n-$, $CH_2=C(R^5)-(CH_2)_m-X^1-C(=O)-(CH_2)_n-$, $CH_2=C(R^5)-(CH_2)_m-C(=O)-X^1-(CH_2)_n-$, $\{CH_2=C(R^5)-(CH_2)_m-\}_2N-(CH_2)_n-$, or $\{CH_2=C(R^5)-(CH_2)_m-\}_2N-C(=O)-(CH_2)_n-$; wherein $X^1$ is —O— or —$NR^6$—, $R^5$ and $R^6$ are independently hydrogen, or linear or branched alkyl of $C_1$–$C_{10}$, and m and n are independently integers of 0 to 10; and formula [II] is represented by the general formula:

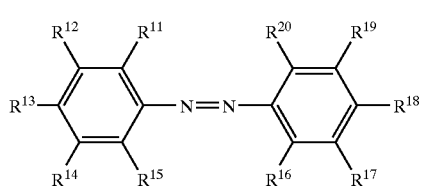

[II]

wherein $R^{11}$, $R^{12}$, $R^{13}$, $R^{14}$, $R^{15}$, $R^{16}$, $R^{17}$, $R^{18}$, $R^{19}$, and $R^{20}$ are independently selected from hydrogen, hydroxy, halogen, or linear or branched alkyl of $C_1$–$C_{10}$, and at least one of them is a substituted group represented by:

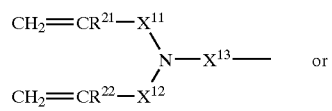 or

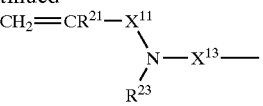

wherein $R^{21}$ and $R^{22}$ are independently hydrogen or methyl, $R^{23}$ is hydrogen or linear or branched alkyl of $C_1$–$C_{10}$, $X^{11}$, $X^{12}$ and $X^{13}$, independently, have covalent bonds, or linear or branched bivalent spacer groups, or —$(CH_2)_m$—O—$(CH_2)_n$—, wherein m and n are independently integers of 0 to 10.

2. The coloring silicone material described in claim 1, in which the silicone having hydrosilyl groups is a dimethylsiloxane-methylhydrosiloxane copolymer.

3. An intraocular lens using the material described in claim 2.

4. The coloring silicone material described in claim 1, which the silicone having hydrosilyl groups is a diphenylsiloxane-phenylhydrosiloxane copolymer.

5. An intraocular lens using the material described in claim 4.

6. The coloring silicone material described in claim 1, in which the silicone having hydrosilyl groups is polyethylhydrosiloxane.

7. An intraocular lens using the material described in claim 6.

8. The coloring silicone material described in claim 1, in which the silicone having hydrosilyl groups is a methylhydrosiloxane-phenylmethylsiloxane copolymer.

9. An intraocular lens using the material described in claim 8.

10. The coloring silicone material described in claim 1, in which the silicone having hydrosilyl groups is a methylhydrosiloxane-octylmethylsiloxane copolymer.

11. An intraocular lens using the material described in claim 10.

12. The coloring silicone material described in claim 1, in which the silicone having hydrosilyl groups is a silicone resin containing hydrosilyl groups.

13. The coloring silicone material described in claim 1, in which the silicone having hydrosilyl groups is polyphenyl (dimethylhydrosiloxy)siloxane.

14. A silicone elastomer obtained from formation by a crosslinking reaction of the silicone having hydrosilyl groups described in claim 1 with a silicone having vinyl groups.

15. An intraocular lens using the material described in claim 14.

16. A silicone elastomer obtained from formation by a crosslinking reaction of the silicone having hydrosilyl groups described in claim 1, a silicone having vinyl groups and a silica.

17. An intraocular lens using the material described in claim 16.

18. An intraocular lens using the material described in claim 1.

19. A coloring silicone material using a material which is obtained from chemical bonding of the dye represented by formula [I] or [II] and an ultraviolet absorber having functional groups capable of chemical bonding, to a silicone having hydrosilyl groups; wherein formula [I] is represented by the general formula:

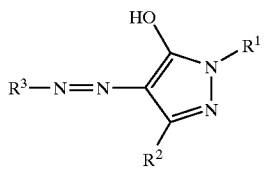

[I]

wherein $R^1$ is linear or branched alkyl of $C_1$–$C_{10}$, or phenyl; when $R^1$ is phenyl, one or more hydrogens of its aromatic ring may be substituted by linear or branched alkyl of $C_1$–$C_{10}$, linear or branched alkoxyl of $C_1$–$C_{10}$, hydroxy, amino, sulfo, nitro, halogen, carboxy, —C(=O)—O—$R^4$ or —C(=O)—NH—$R^4$, wherein $R^4$ is linear or branched alkyl of $C_1$–$C_{10}$, $R^2$ is linear or branched alkyl of $C_1$–$C_{10}$, amino or phenyl; when $R^2$ is amino, one or both hydrogens thereof may be substituted by linear or branched alkyl of $C_1$–$C_{10}$; or when $R^2$ is phenyl, one or more hydrogens of its aromatic ring may be substituted by linear or branched alkyl of $C_1$–$C_{10}$, linear or branched alkoxyl of $C_1$–$C_{10}$, hydroxy, amino, sulfo, nitro, halogen, carboxyl, —C(=O)—O—$R^4$, —C(=O)—NH—$R^4$ wherein $R^4$ is linear or branched alkyl of $C_1$–$C_{10}$, $R^3$ is phenyl or naphthyl, one or more hydrogens thereof are linear or branched alkyl of $C_1$–$C_{10}$, linear or branched alkoxyl of $C_1$–$C_{10}$, hydroxy, amino, sulfo, nitro, halogen, carboxy, —C(=O)—O—$R^4$, —C(=O)—NH—$R^4$, wherein $R^4$ is linear or branched alkyl of $C_1$–$C_{10}$, and in formula [I], at least one hydrogen of the aromatic ring constituted in $R^1$, $R^2$ or $R^3$ is substituted by any of $CH_2$=CH—$(CH_2)_m$—, $CH_2$=CH—$(CH_2)_m$—$X^1$—$(CH_2)_n$—, $CH_2$=C($R^5$)—$(CH_2)_m$—$X^1$—C(=O)—$(CH_2)_n$—, $CH_2$=C($R^5$)—$(CH_2)_m$—C(=O)—$X^1$—$(CH_2)_n$—, {$CH_2$=C($R^5$)—$(CH_2)_m$—}$_2$N—$(CH_2)_n$—, or {$CH_2$=C($R^5$)—$(CH_2)_m$—}$_2$N—C(=O)—$(CH_2)_n$—; wherein $X^1$ is —O— or —$NR^6$—, $R^5$ and $R^6$ are independently hydrogen, or linear or branched alkyl of $C_1$–$C_{10}$, and m and n are independently integers of 0 to 10; and formula [II] is represented by the general formula:

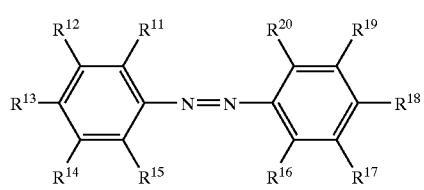

[II]

wherein $R^{11}$, $R^{12}$, $R^{13}$, $R^{14}$, $R^{15}$, $R^{16}$, $R^{17}$, $R^{18}$, $R^{19}$, and $R^{20}$ are independently selected from hydrogen, hydroxy, halogen, or linear or branched alkyl of $C_1$–$C_{10}$, and at least one of them is a substituted group represented by:

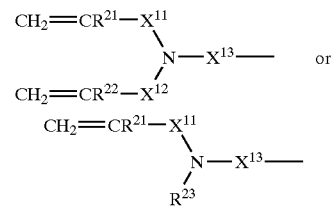

wherein $R^{21}$ and $R^{22}$ are independently hydrogen or methyl, $R^{23}$ is hydrogen or linear or branched alkyl of $C_1$–$C_{10}$, $X^{11}$, $X^{12}$ and $X^{13}$, independently, have covalent bonds, or linear or branched bivalent spacer groups, or —$(CH_2)_m$—O—$(CH_2)_n$—, wherein m and n are independently integers of 0 to 10.

20. The coloring silicone material described in claim 19, in which the silicone having hydrosilyl groups is a dimethylsiloxane-methylhydrosiloxane copolymer.

21. An intraocular lens using the material described in claim 20.

22. The coloring silicone material described in claim 19, in which the silicone having hydrosilyl groups is a diphenylsiloxane-phenylhydrosiloxane copolymer.

23. An intraocular lens using the material described in claim 22.

24. The coloring silicone material described in claim 19, in which the silicone having hydrosilyl groups is polyethylhydrosiloxane.

25. An intraocular lens using the material described in claim 24.

26. The coloring silicone material described in claim 19, in which the silicone having hydrosilyl groups is a methylhydrosiloxane-phenylmethylsiloxane copolymer.

27. An intraocular lens using the material described in claim 26.

28. The coloring silicone material described in claim 19, in which the silicone having hydrosilyl groups is a methylhydrosiloxane-octylmethylsiloxane copolymer.

29. The coloring silicone material described in claim 19, in which the silicone having hydrosilyl groups is a silicone resin containing hydrosilyl groups.

30. The coloring silicone material described in claim 19, in which the silicone having hydrosilyl groups is polyphenyl (dimethylhydrosiloxy)siloxane.

31. A silicone elastomer obtained from formation by a crosslinking reaction of the silicone having hydrosilyl groups described in claim 19 with a silicone having vinyl groups.

32. An intraocular lens using the material described in claim 31.

33. A silicone elastomer obtained from formation by a crosslinking reaction of the silicone having hydrosilyl groups described in claim 19, a silicone having vinyl groups and a silica.

34. An intraocular lens using the material described in claim 33.

35. An intraocular lens using the material described in claim 19.

* * * * *